United States Patent [19]

Bollag et al.

[11] Patent Number: 5,428,071

[45] Date of Patent: Jun. 27, 1995

[54] PREVENTION AND TREATMENT OF PREMALIGNANT EPITHELIAL LESIONS AND MALIGNANT TUMORS OF EPITHELIAL ORIGIN

[75] Inventors: Werner Bollag, Basel, Switzerland; Joseph F. Grippo, Basking Ridge; Arthur Levin, Glen Ridge, both of N.J.

[73] Assignee: Hoffmann-La Roche Inc., Nutley, N.J.

[21] Appl. No.: 201,493

[22] Filed: Feb. 24, 1994

Related U.S. Application Data

[63] Continuation of Ser. No. 823,741, Jan. 22, 1992, abandoned.

[51] Int. Cl.$^6$ .............................................. A61K 31/20
[52] U.S. Cl. .................................................. 514/559
[58] Field of Search ........................................ 514/559

[56] References Cited

FOREIGN PATENT DOCUMENTS 1335867 10/1973 United Kingdom ................ 514/559

Primary Examiner—Jerome D. Goldberg
Attorney, Agent, or Firm—George M. Gould; William H. Epstein

[57] ABSTRACT

The compound 9-cis-retinoic acid, its pharmaceutically acceptable salts or its pharmaceutically acceptable esters can be used in the treatment of precancerous or premalignant epithelial lesions as well as in the treatment of malignant tumors of an epithelial nature.

14 Claims, No Drawings

PREVENTION AND TREATMENT OF PREMALIGNANT EPITHELIAL LESIONS AND MALIGNANT TUMORS OF EPITHELIAL ORIGIN

This is a continuation of application Ser. No. 07/823,741 filed Jan. 22, 1992, now abandoned.

BACKGROUND OF INVENTION

Retinoids play an essential role in controlling the normal growth and differentiation of various tissues and are therefore important for prevention and treatment of premalignant and malignant lesions. It has even been found that retinoids can cause cellular repair of hyperplastic, metaplastic and dsyplastic lesions caused by carcinogens. Moreover, retinoid deficiency has been shown to enhance susceptibility to chemical carcinogenesis. Indeed, retinoids are essential for the normal cellular growth and differentiation of epithelial tissues where more than half of the total primary cancers develop in both men and women. These epithelial tissues include the mouth, bronchi, larynx, pharynx, breast, esophagus, stomach, colon, uterus, kidney, bladder, testis, prostate, pancreatic ducts and skin. In the absence of retinoids in the diet, normal cellular growth and differentiation is disturbed.

The developments in this field, which are summarized above, are discussed in an article entitled "Prevention of chemical Carcinogenesis by Vitamin A and its Synthetic Analogs (Retinoids)", Federation Proceedings, 35, (May 1, 1976), 1332–1338.

While retinoid-type compounds have been found to be effective in treating carcinomas, and inhibiting the progression of premalignant or precancerous lesions to carcinomas, many of these retinoids have high toxicity and produce deleterious adverse effects such as hypervitaminosis A. The toxicity and adverse effect profile of many of these retinoids make them unsuitable for use in the treatment and prevention of cancer at high dosage levels where their effects are greatest. Therefore, it is desired to provide a retinoid type compound which will exhibit the tumor inhibiting effect of retinoids without the toxic manifestation or adverse effects generally associated with such retinoids.

SUMMARY OF THE INVENTION

In accordance with this invention, the topical and oral administration of 9-cis retinoic acid in patients, which compound has the formula:

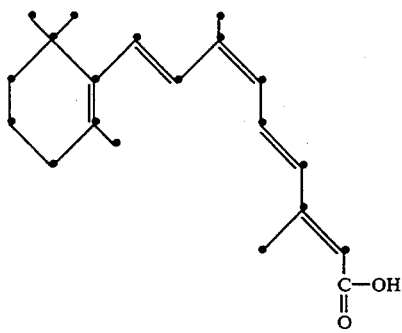

its pharmaceutically acceptable salts and its pharmaceutically acceptable hydrolyzable esters, are effective in treating patients bearing premalignant or precancerous epithelial lesions to reverse the progression of these lesions into carcinomas. The compound of formula I, its pharmaceutically acceptable esters, and its pharmaceutically acceptable salts are also effective in treating tumors of an epithelial origin in patients to retard the development of these tumors.

DETAILED DESCRIPTION

In accordance with this invention, it has been found that the compound of formula I, its pharmaceutically acceptable salts or its pharmaceutically acceptable hydrolyzable esters possesses with the regard to epithelial lesions, antihyperplastic, antimetaplastic, antineoplastic tumor-preventative and tumor-therapeutic properties exhibiting limited toxicity or other adverse effects associated with retinoids. It has now been found that pathological conditions which involve the above properties can be effectively treated by administering the compound of formula I, its pharmaceutically acceptable salts or its pharmaceutically acceptable hydrolyzable esters either systemically or topically.

In accordance with one embodiment of this invention, the compound of formula I, its pharmaceutically acceptable salts or its pharmaceutically acceptable hydrolyzable esters when administered to mammals having premalignant epithelial lesions, i.e., precancerous lesions, retards the progression of the lesions. This compound controls the cellular growth and differentiation of these premalignant or precancerous lesions and causes cellular repair. In this way, the development of these lesions into epithelial carcinomas is prevented.

In treating premalignant or precancerous epithelial lesions to retard the progression of these lesions into carcinomas, the compound of formula I, its pharmaceutically acceptable salts or its pharmaceutically acceptable hydrolyzable esters is administered either orally or topically to patients affected by these lesions in an amount effective for retarding the progression of these lesions. The amount will be dependent on the amount and size of the lesions and on the requirement of the patient. In administering this compound to a patient for treating premalignant or precancerous epithelial lesions to retard the progression of these lesions into carcinomas.

The compound of formula I its pharmaceutically acceptable salts or its pharmaceutically acceptable hydrolyzable esters is especially effective in treating premalignant or precancerous lesions of an epithelial nature. This compound is effective in treating premalignant or precancerous lesions of the breast, skin, colon, bladder, esophagus, stomach, larynx, lung or oral cavity. In accordance with a preferred embodiment, this compound can be utilized to treat premalignant or precancerous lesions such as various leukoplakias, especially that of the mouth and tongue, as well as precancerous or premalignant lesions of the breast.

In accordance with a further embodiment of this invention, the compound of formula I, its pharmaceutically acceptable salts or its pharmaceutically acceptable hydrolyzable esters can be utilized to treat carcinomas or tumors of epithelial origin to retard the development of these tumors. In accordance with the anti-carcinoma or anti-tumor properties of this compound, treatment of the tumors with this compound produces a regression in both the size and number of these tumors. In utilizing this compound as an anti-tumor agent, this compound is especially effective in retarding the development of tumor of the breast, skin, colon, bladder, esophagus, stomach, larynx, lung or mouth. The compound of formula I can be administered to patients in the manner described above in connection with treating patients having premalignant or precancerous lesions.

For the treatment given above, the compound of formula I its pharmaceutically acceptable salts or its pharmaceutically acceptable hydrolyzable esters is administered either systemically or topically as a composition containing the compound of formula I and a pharmaceutically acceptable carrier compatible with said compound. In preparing such composition, any conventional pharmaceutically acceptable carrier can be utilized. When the drug is administered orally, it is generally administered at regular intervals, conveniently at mealtimes or once daily. It has been established that this compound is relatively non-toxic when given topically and when given orally.

Examples of conditions involving premalignant and precancerous epithelial lesions or tumors which are effectively treated with the compound of formula I are actinic keratoses, arsenic keratoses, xeroderma pigmentosum, Bowen's disease, leukoplakias, metaplasias, dysplasias and papillomas of mucous membranes, e.g. of the mouth, tongue, pharynx and larynx, precancerous changes of the bronchial mucous membrane such as metaplasias and dysplasias (especially frequent in heavy smokers and people who work with asbestos and/or uranium), dysplasias and leukoplakias of the cervix uteri, vulval dystrophy, precancerous changes of the bladder, e.g. metaplasias and dysplasias, papillomas of the bladder as well as polyps of the intestinal tract. Examples of tumors or carcinomas of semi-malignant or malignant nature, of the epithelial origin which are effectively treated by the compound of formula I are breast tumors, skin tumors, e.g. basal cell carcinomas, bladder tumors, e.g. superficial bladder carcinomas, colon tumors, esophageal tumors, stomach tumors, laryngeal tumors and lung tumors.

The treatment of precancerous lesions and malignant tumors of epithelial nature can be effected with the compound of formula I its pharmaceutically acceptable salts or its pharmaceutically acceptable hydrolyzable esters alone or in combination with other measures such as surgery, radiation therapy, hormone therapy or treatment with standard chemotherapy (cytostatic and cytotoxic agents) or biological response modifiers (interferons, interleukins, agents or other cytokines).

The pharmaceutically acceptable salts includes any salt chemically permissible in the art for 9-cis-retinoic acid and applicable to human patients in a pharmaceutically acceptable preparation. Any such conventional pharmaceutically acceptable salt of the compounds of formula I can be utilized. Among the conventional salts which can be utilized there are the base salts included, for example, alkali metal salts such as sodium or potassium, alkaline earth metal salts such as sodium or potassium, alkaline earth metal salts such as calcium or magnesium, and ammonium or alkyl ammonium salts.

In accordance with this invention the 9-cis-retinoic acid can be administered in the form of its pharmaceutically acceptable hydrolyzable esters. Any pharmaceutically acceptable hydrolyzable ester can be used in the compositions and methods of this invention. Among the esters are the aromatic esters such as benzyl (OBzl) or benzyl substituted with lower alkyl, halo, nitro, thio, or substituted thio, i.e., lower alkyl, t-butyl, cyclopentyl, cyclohexyl, cycloheptyl, and 9-fluorenylmethyl.

In accordance with this invention, the aforementioned compound or formula I or its pharmaceutically acceptable salts and its pharmaceutically acceptable hydrolyzable esters are useful in pharmaceutically acceptable oral or topical modes. These pharmaceutical compositions of the invention contain said compound for formula I or its pharmaceutically acceptable salts and its pharmaceutically acceptable hydrolyzable esters in association with a compatible pharmaceutically acceptable carrier material. Any conventional carrier material can be utilized. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: (a) a solid form for oral administration such as tablets, capsules, pills, powders, granules, and the like; and (b) preparations for topical administrations such as solutions, suspensions, ointments, creams, gels, micronized powders, aerosols and the like. The pharmaceutical preparations may be sterilized and/or may contain adjuvants such as preservatives, stablizers, wetting agents, emulsifiers, salts for varying the osmotic pressure and/or buffers.

For topical administration to the skin the aforementioned derivative is preferably prepared as ointments, tinctures, creams, gels, solutions, lotions, sprays, suspensions, shampoos, hair soaps, perfumes and the like. In fact, any conventional composition utilized this invention. Among the preferred methods of applying the composition containing the agents of this invention is in the form of a gel, lotion and cream. The pharmaceutical preparation for topical administration to the skin can be prepared by mixing the aforementioned active ingredient with non-toxic, therapeutically inert, solid or liquid carriers customarily used in such preparations. These preparations should contain at least about 0.01 percent by weight, of the active ingredient based upon the total weight of the composition. Since the active ingredient, the compound of formula I, is relatively non-toxic, and non-irritating it may be used in topical compositions in amounts exceeding 0.15% percent. It is preferred that these preparations contain about 0.01 to 0.15% percent by weight of the active ingredient based upon the total weight of the composition. It is also preferred to apply these preparations once or twice daily to the skin. These preparations can be applied according to the need of the patient. In carrying out this invention, the active ingredient can be applied in an aqueous solution or an alcohol solution such as ethyl alcohol.

In preparing the topical preparations described above additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-a-tocopherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, 1,2oethyleneglycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid at least about 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

A preferred oral dosage form comprises tablets, capsules of hard or soft gelatin methylcellulose or of another suitable material easily dissolved in the digestive tract. The oral dosages contemplated in accordance with the present invention will vary in accordance with the needs of the individual patient as determined by the prescribing physician. Generally, however, a daily dosage of from about 0.01 mg. to about 3 mg per Kg of body weight and preferably from about 0.025 mg to about 1.5 mg per Kg of body weight of the patient is utilized. This dosage may be administered according to any dosage schedule determined by the physician in accordance with the requirements of the patient.

It is likewise within the preview of the present invention to incorporate the therapeutically active substance enumerated herein in any desired amount for enteral administration within the oral unit dosage form. It is preferred, however, to formulate preparations containing the active substance of the present invention in such a manner that each dose forms contains from about 1 mg to about 50 mg with suitable therapeutically inert fillers and diluents. It is especially preferred to incorporate such a dosage into soft gelatin capsules and tablets.

The dosage for treatment typically depends on the route of administration, the age, weight and acne condition of the individual. The following examples illustrate pharmaceutical preparations containing the 9-cis-retinoic acid as provided by the present invention. The compound 9-cis-retinoic acid can also be designated by the name (E, Z, E, E)-3,7-dimethyl-9-[2, 6, 6-trimethyl-1-cyclohexen-1-yl]-2, 4, 6, 8-nonatetraenoic acid.

EXAMPLE 1

| Lotion (solution) | | preferred |
|---|---|---|
| 9-cis-Retinoic Acid | 0.02–0.30 g | |
| Propylene Glycol | 5.00–20.00 g | 10.00 g |
| PEG-Glyceryl Cocoate* | 0.00–20.00 g | 10.00 g |
| dl-α-Tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr** | 0.00–0.20 g | 0.01 g |
| Isopropanol*** | 40.00–90.00 g | 50.00 g |
| Water, dem. ad | 100.00 g | 100.00 g (resp. ml) |

*or other tensides
**or other complexing agents e.g. EDTA
***or other alcohols e.g., Ethanol

EXAMPLE 2

| Gel | | preferred |
|---|---|---|
| 9-cis-Retinoic Acid | 0.02–0.30 g | |
| Propylene Glycol | 5.00–20.00 g | 10.00 g |
| PEG-Glyceryl Cocoate* | 0.00–20.00 g | 10.00 g |
| dl-α-Tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr** | 0.00–0.20 g | 0.01 g |
| Isopropanol*** | 40.00–90.00 g | 50.00 g |
| HPMC**** | 0.50–5.00 g | 3.00 g |
| Preservative***** | q.s. | q.s. |
| Water, dem. ad | 100.00 g | 100.00 g |

*or other tensides
**or other complexing agents e.g. EDTA
***or other alcohols e.g., Ethanol
****Hydroxypropyl Methylcellulose or other polymers e.g. neutralized Carbomer, Methyl Cellulose, Sodium Carboxymethylcellulose
*****Preservatives e.g., Paraben esters (methyl, ethyl, propyl, butyl), Sorbic Acid, Benzoic, Acid

EXAMPLE 3

| Cream | | preferred |
|---|---|---|
| 9-cis-Retinoic Acid | 0.02–0.30 g | |
| Glycerol | 0.00–10.00 g | 5.00 g |
| Na₂EDTA | 0.001–0.50 g | 0.03 g |
| Glycerides* | 5.00–20.00 g | 10.00 g |
| Cetyl Alcohol | 0.50–5.00 g | 1.00 g |
| Stearyl Alcohol | 0.50–5.00 g | 1.00 g |
| Glycerol mono Stearate | 1.00–8.00 g | 4.00 g |
| Cetaereth** | 0.50–5.00 g | 2.00 g |
| dl-α-Tocopherol | 0.001–0.50 g | 0.02 g |
| Preservative*** | q.s. | q.s. |
| Water, dem. ad | 100.00 g | 100.00 g |

*e.g. Caprylic/Capric/Triglyceride, Caprylic/Capric/Linoleic Triglyceride, natural glycerides, as well as e.g., Propylene Glycol, Dicaprylate/Dicaprate and waxes such as Stearyl Stearate, Oleyl Oleate, Isopropyl Myristate.
**Ceteareth 5-30, or other emulsifiers such as Polysorbate 20-80, Sorbitane esters of fatty acids, fatty acid esters of PEG.
***Preservatives e.g., Paraben esters (methyl, ethyl, propyl, butyl), Sorbic Acid, Benzoic Acid.

EXAMPLE 4

Fill mass for soft gelatin capsules

| 9-cis-Retinoic Acid | 5.00–50.00 mg |
|---|---|
| Oil* | 1–3 parts |
| Wax mixture** | 1–5 parts |
| Fill volume | 1–6 minims |

*natural vegetable oils, e.g., soy oil, peanut oil, and artificial glycerides
**composition of natural and artificial waxes or partially hydrated fats

EXAMPLE 5

1. Hard Gelatine capsules containing 20 mg, active substance:

| Composition: One Capsule contains: | |
|---|---|
| 9-cis-Retinoic acid | 20.0 mg. |
| Gelatine Bloom 30 | 70.0 mg. |
| Maltodextrin MD 05 | 108.0 mg. |
| dl-α-Tocopherol | 2.0 mg. |
| Sodium ascorbate | 10.0 mg. |
| Microcrystalline cellulose | 48.0 mg. |
| Magnesium stearate | 2.0 mg. |
| (weight capsule content) | 260.0 mg. |

EXAMPLE 5

1. Hard Gelatine capsules containing 20 mg, active substance:

Procedure:

The active substance is wet milled in a solution of gelatine, maltodextrin, dl-α-Tocopherol and sodium ascorbate.
The wet milled suspension is spray-dried
The spray-dried powder is mixed with microcrystalline cellulose and magnesium stearate.
260 mg. each of this mixture are filled into hard gelatine capsules of suitable size and color.

EXAMPLE 6

2. Tablet containing 20 mg active substance:

| Composition: | |
|---|---|
| Tablet kernel: | |
| 9-cis-Retinoic acid | 20.0 mg. |
| Anhydrous lactose | 130.5 mg. |
| Microcrystalline Cellulose | 80.0 mg. |
| dl-α-Tocopherol | 2.0 mg. |
| Sodium ascorbate | 10.0 mg. |
| Polyvinylpyrrolidone K30 | 5.0 mg. |
| Magnesium stearate | 2.5 mg. |
| (Kernel weight) | 250.0 mg. |
| Film coat: | |
| Hydroxypropyl methylcellulose | 3.5 mg. |
| Polyethylenglycol 6000 | 0.8 mg. |
| Talc | 1.3 mg. |
| Iron oxide, yellow | 0.8 mg. |
| Titanium dioxide | 0.8 mg. |
| (weight of the film) | 7.4 mg. |

Procedure:

9-cis-Retinoic acid is mixed with anhydrous lactose and microcrystalline cellulose.
The mixture is granulated in water with a solution/dispersion of polyvinylpyrrolidone, dl-α-Tocopherol and sodium ascorbate.
The granular material is mixed with magnesium stearate and afterwards pressed as kernels with 250 mg. weight.
The kernels are film coated with a solution/suspension of above-mentioned composition.

EXAMPLE 7

Sachet containing 50 mg, active substance

| Composition: | |
|---|---|
| 9-cis-Retinoic acid | 50.0 mg. |
| Lactose, fine powder | 990.0 mg. |
| Microcrystalline Cellulose | 1400.0 mg. |
| Sodium Carboxymethyl-cellulose | 14.0 mg. |
| dl-α-Tocopherol | 5.0 mg. |
| Sodium ascorbate | 20.0 mg. |
| Polyvinylpyrrolidone K30 | 10.0 mg. |
| Magnesium stearate | 10.0 mg. |
| Flavouring Agents | 1.0 mg. |
| (Fill weight of a sachet) | 2500.0 mg. |

Procedure:

9-cis-Retinoic acid is mixed with lactose, microcrystalline cellulose and sodium carboxymethyl cellulose.
The mixture is granulated in water with a solution/dispersion of polyvinylpyrrolidone, dl-α-Tocopherol and sodium ascorbate.
The granule is mixed with magnesium stearate and flavoring agents.

EXAMPLE 7

Sachet containing 50 mg, active substance

It is filled into sachets of suitable size.

We claim:

1. A method for treating patients having premalignant or precancerous epithelial lesions to retard the progression of these lesions into carcinomas comprising administering to said patient a composition containing a compound selected from the group consisting of 9-cis-retinoic acid, its pharmaceutically acceptable salts, and its pharmaceutically acceptable hydrolyzable esters said compound being administered in an amount effective to treat said lesions.

2. The method of claim 1 wherein said composition is administered orally.

3. The method of claim 2 wherein compound is administered at a daily amount dose of from 0.01 mg to 3 mg per kg body weight.

4. The method of claim 3 wherein said lesions are leukoplakias of the oral cavity.

5. The method of claim 3 wherein said composition is administered in an oral unit dosage form containing 1 mg to 50 mg of the compound.

6. The method of claim 5 wherein said oral unit dosage form is a capsule or tablet.

7. A method for treating tumors of epithelial origin in patients to retard the development of these tumors comprising administering to said patient a composition containing a compound selected from the group consisting of 9-cis-retinoic acid, its pharmaceutically acceptable salts, and its pharmaceutically acceptable hydrolyzable esters, said compound being administered in an amount effective to retard the development of said tumors.

8. The method of claim 7 wherein said composition is administered orally.

9. The method of claim 8 wherein said compound is administered at a daily dose of from 0.01 mg to 3 mg per kg body weight.

10. The method of claim 9 wherein said tumors are selected from the group consisting of epithelial tumors of the breast, skin, colon, bladder, esophagus, stomach, larynx, lung or oral cavity.

11. The method of claim 9 wherein said composition is administered in an oral unit dosage form containing 1 mg to 50 mg of the compound.

12. The method of claim 11 wherein said oral unit dosage form is a capsule or tablet.

13. The method of claim 10 wherein said tumors are tumors of the breast.

14. A composition in unit dosage form for oral administration comprising as an active ingredient a compound selected from the group consisting of 9-cis retinoic acid, pharmaceutically acceptable salts thereof and pharmaceutically acceptable hydrolyzable esters thereof and a pharmaceutically acceptable carrier suitable for oral administration, said active ingredient being present in said unit dosage form in an amount of from about 1 mg to 50 mg wherein said unit dosage form is a tablet or capsule.

* * * * *